US012570637B2

(12) United States Patent
Roberts et al.

(10) Patent No.: US 12,570,637 B2
(45) Date of Patent: Mar. 10, 2026

(54) CRYSTALLINE SALT FORMS 6-(CYCLOPROPANECARBOXAMIDO)-4-((2-METHOXY-3-(1-METHYL-1H-1,2,4-TRIAZOL-3-YL)PHENYL)AMINO)-N-(METHYLD3) PYRIDAZINE-3-CARBOXAMIDE

(71) Applicant: Bristol-Myers Squibb Company, Princeton, NJ (US)

(72) Inventors: Daniel Richard Roberts, Robbinsville, NJ (US); Chenkou Wei, Princeton Junction, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 922 days.

(21) Appl. No.: 17/617,003

(22) PCT Filed: Jun. 9, 2020

(86) PCT No.: PCT/US2020/036727

§ 371 (c)(1),
(2) Date: Dec. 7, 2021

(87) PCT Pub. No.: WO2020/251911

PCT Pub. Date: Dec. 17, 2020

(65) Prior Publication Data

US 2022/0235039 A1 Jul. 28, 2022

Related U.S. Application Data

(60) Provisional application No. 62/860,439, filed on Jun. 12, 2019.

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .......................... C07D 403/12; C07B 2200/13
See application file for complete search history.

(56) References Cited

U.S. PATENT DOCUMENTS

| | | | |
|---|---|---|---|
| 9,505,748 | B2 | 11/2016 | Moslin et al. |
| 2010/0298315 | A1 | 11/2010 | Albert et al. |
| 2011/0237576 | A1 | 9/2011 | Yonezawa et al. |

FOREIGN PATENT DOCUMENTS

| | | | |
|---|---|---|---|
| WO | WO-2018/183649 | A1 | 10/2018 |
| WO | WO-2018/183656 | A1 | 10/2018 |
| WO | WO-2019/232138 | A1 | 12/2019 |

OTHER PUBLICATIONS

Bhattacharya et al., Polymorphism in Pharmaceutical Solids: Thermoanalytical and Crystallographic Methods 334 (Brittain H. ed., 2d ed. Informa Healthcare USA, Inc. 2009) (1999) (Year: 1999).*
Ivanisevic, I., Pharm. Form. Qual. 30-33, 32 (2011) (Year: 2011).*
Caira, Mino R., Crystalline Polymorphism of Organic Compounds, In: Weber E et al. (eds.), Topics in Current Chemistry, vol. 198, pp. 163-208, Springer Verlag, Berlin Heidelberg 1998.
Stahl, P. Heinrich; Wermuth, Camille G. (eds.), Handbook of Pharmaceutical Salts: Properties, Selection, and Use, pp. 329-350, 2002.
International Search Report and Written Opinion for PCT/US2020/036727 dated Aug. 31, 2020.
Kazuhide Ashizawa, Polymorphism and crystallization of the pharmaceutical drugs, Maruzen Planet Co., Ltd., 2002, pp. 305-317.

* cited by examiner

*Primary Examiner* — Timothy R Rozof
(74) *Attorney, Agent, or Firm* — Covington & Burling LLP

(57) ABSTRACT

Disclosed are crystalline salt Forms C and D of 6-(cyclopropanecarboxamido)-4-((2-methoxy-3-(1-methyl-1H-1,2,4-triazol-3-yl)phenyl)amino)-N-(methyl-d3)pyridazine-3-carboxamide. Form C is a MSA salt and Form D is a sulfate salt of Compound (I). Characterization data for the Forms are disclosed.

(I)

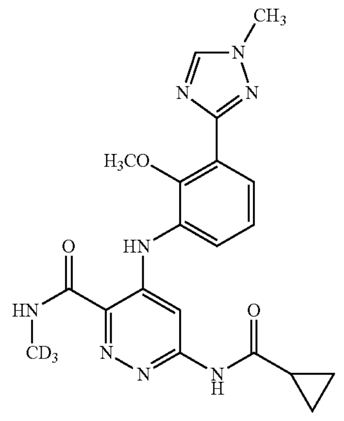

13 Claims, 7 Drawing Sheets

CRYSTALLINE SALT FORMS 6-(CYCLOPROPANECARBOXAMIDO)-4-((2-METHOXY-3-(1-METHYL-1H-1,2,4-TRIAZOL-3-YL)PHENYL)AMINO)-N-(METHYLD3) PYRIDAZINE-3-CARBOXAMIDE

CROSS-REFERENCE TO RELATED APPLICATIONS

This application claims the benefit of U.S. Provisional Application No. 62/860,439, filed Jun. 12, 2019, the disclosure of which is incorporated herein by reference in its entirety.

FIELD OF THE INVENTION

The present invention generally relates to crystalline salt forms of 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide, hereinafter referred to as "Form C" and "Form D", respectively. Form C is a MSA salt and Form D is a sulfate salt of the compound.

BACKGROUND OF THE INVENTION

The compound, 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide, has the structure of Formula (I):

(I)

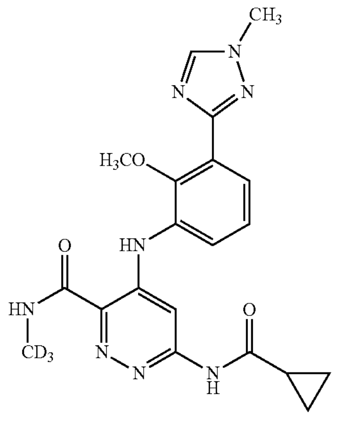

and is referred to herein as "Compound (I)". Compound (I) is disclosed U.S. Pat. No. 9,505,748 B2, which is assigned to the present assignee. U.S. Pat. No. 9,505,748 B2 also discloses methods of treatment employing Compound (I).

Compound (I) is a Tyk2 inhibitor currently in clinical trials for the treatment of auto-immune and auto-inflammatory diseases such as psoriasis, psoriatic arthritis, lupus, lupus nephritis, Sjögren's syndrome, inflammatory bowel disease, Crohn's disease and ankylosing spondylitis.

In the synthesis of a chemical compound intended for pharmaceutical use, it is necessary to isolate and purify the compound at the completion of the synthetic process and prior to further processing to provide the compound in a pharmaceutical formulation. The isolation and the purification steps, which can be combined or separate consecutive steps, provide the compound as a purified solid with minimal loss of yield during isolation from other components of the reaction mixture and/or during purification to remove impurities from the isolated compound sample.

It is desirable to provide a solid form that can be reproducibly produced from the isolation and/or purification steps.

Further, it is desirable to isolate the purified compound in a solid form that is physically and chemically stable at a range of storage conditions, such as at different conditions of temperature and humidity.

Furthermore, it is desirable to provide a compound in a solid form that has sufficient solubility in solvents/solutions to permit preparation of other solid forms.

Further, the Applicants have found a crystalline form of Compound (I) that surprisingly provides Compound (I) in a solid form that is physically and chemically stable at a range of storage conditions, and has sufficient solubility in solvents/solutions to permit preparation of other solid forms.

Further, the Applicants have found a crystalline form of Compound (I) that surprisingly provides Compound (I) in a solid form that mitigates pH effects better than other salts tested.

The present invention is also directed to other important aspects.

SUMMARY OF THE INVENTION

The present invention provides crystalline Form C and Form D of Compound (I). The name used herein to characterize a specific form, e.g. "Form C or Form D" etc., should not be considered limiting with respect to any other substance possessing similar or identical physical and chemical characteristics, but rather it should be understood that this designation is a mere identifier that should be interpreted according to the characterization information also presented herein.

DETAILED DESCRIPTION OF THE INVENTION

Figure 1:
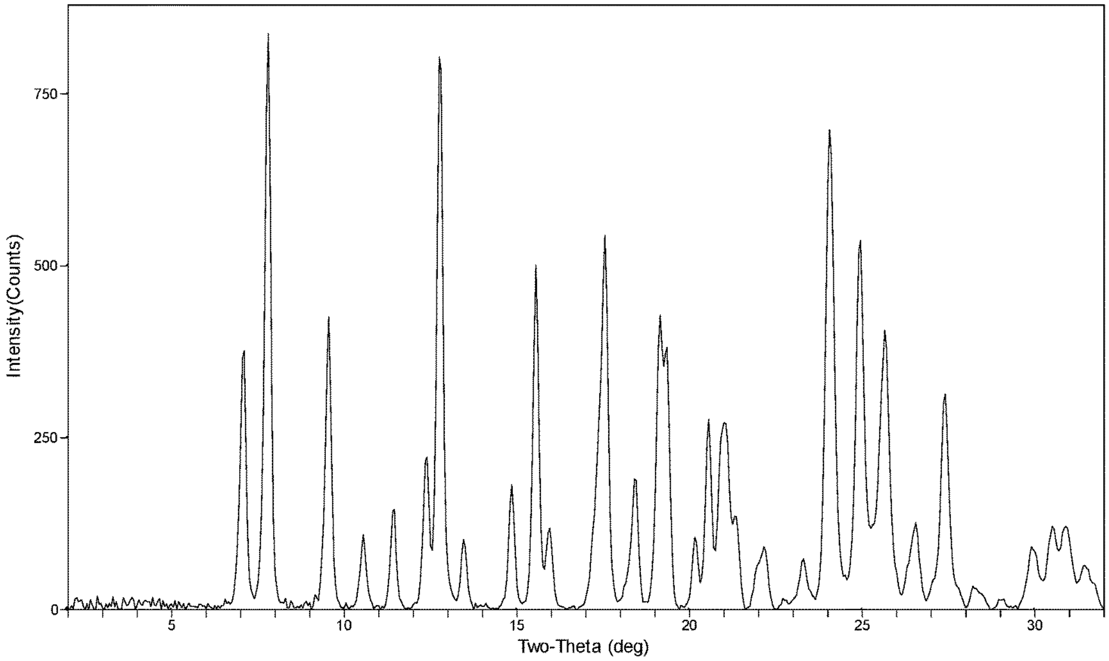
FIG. 1. shows the observed powder x-ray diffraction pattern (CuKα, at T=25° C.) of crystalline Form C of Compound (I).

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "Form C" etc., are merely identifiers that are to be interpreted in accordance with the characterization information presented herein and are not to be limited so as to exclude any other substance possessing similar or identical physical and chemical characteristics.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error and are within the spirit of the invention.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein, "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of Compound (I), based on the weight of the compound. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises amorphous and/or other form(s) of Compound (I) and/or reaction impurities and/or processing impurities.

As used herein, a powder x-ray diffraction (PXRD) pattern "comprising" a number of peaks selected from a specified group of peaks, is intended to include PXRD patterns having additional peaks that are not included in the specified group of peaks. For example, a PXRD pattern comprising four or more, preferably five or more, 2θ values selected from: A, B, C, D, E, F, G, and H, is intended to include a PXRD pattern having: (a) four or more, preferably five or more, 2θ values selected from: A, B, C, D, E, F, G, and H; and (b) zero or more peaks that are not one of peaks A, B, C, D, E, F, G, and H.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the unit cell parameter "molecules per unit cell" refers to the number of molecules of Compound (I) in the unit cell.

Form C of Compound (I)

In one embodiment, Compound (I) is provided as a crystalline material comprising Form C. The crystalline Form C of Compound (I) is an MSA salt.

TABLE 1

| $^{13}C$ CPMAS chemical shift values of Form C at 280K ppm (±0.2) |
|---|
| 177.8 |
| 163.2 |
| 159.8 |
| 151.2 |
| 146.3 |
| 136.0 |
| 132.9 |
| 127.0 |
| 124.7 |
| 123.8 |
| 121.1 |
| 97.5 |
| 63.5 |
| 40.3 |
| 36.7 |
| 24.2 |

In one embodiment, crystalline Form C of Compound (I) is characterized by a powder x-ray diffraction pattern comprising four or more 2θ values in degrees (CuKα) selected from: 7.1±0.2; 7.8±0.2; 9.5±0.2, 10.6±0.2; 11.4±0.2; 12.8±0.2; 15.6±0.2; 17.5±0.2 and 24.1±0.2, wherein the PXRD pattern of Form C is measured at a temperature of about 25° C.;

In one embodiment, crystalline Form C of Compound (I) is characterized by a powder x-ray diffraction pattern comprising five or more 2θ values in degrees (CuKα) selected from: 7.1±0.2; 7.8±0.2; 9.5±0.2, 10.6±0.2; 11.4±0.2; 12.8±0.2; 15.6±0.2; 17.5±0.2 and 24.1±0.2, wherein the PXRD pattern of Form C is measured at a temperature of about 25° C.;

In one embodiment, crystalline Form C of Compound (I) is characterized by a powder x-ray diffraction pattern comprising six or more 2θ values in degrees (CuKα) selected from: 7.1±0.2; 7.8±0.2; 9.5±0.2, 10.6±0.2; 11.4±0.2; 12.8±0.2; 15.6±0.2; 17.5±0.2 and 24.1±0.2, wherein the PXRD pattern of Form C is measured at a temperature of about 25° C.;

In one embodiment, crystalline Form C of Compound (I) is characterized by a powder x-ray diffraction pattern comprising 2θ values in degrees (CuKα) at 7.8±0.2 and 9.5±0.2; and three or more 2θ values in degrees (CuKα) selected from: 7.1±0.2; 10.6±0.2; 11.4±0.2; 12.8±0.2; 15.6±0.2; 17.5±0.2 and 24.1±0.2; wherein the PXRD pattern of Form C is measured at a temperature of about 25° C.

In one embodiment, crystalline Form C of Compound (I) is characterized by a $^{13}C$ ssNMR spectrum comprising four or more chemical shift values in ppm (all±0.2) selected from: 177.8; 163.2; 159.8; 151.2; 146.3; 136.0; 132.9; 127.0; 124.7; 123.8; 121.1; 97.5; 63.5; 40.3; 36.7 and 24.2; wherein the spectrum of Form C is measured at a temperature of about 280 K.

In one embodiment, crystalline Form C of Compound (I) is characterized by a $^{13}C$ ssNMR spectrum comprising five or more chemical shift values in ppm (all±0.2) selected from: 177.8; 163.2; 159.8; 151.2; 146.3; 136.0; 132.9; 127.0; 124.7; 123.8; 121.1; 97.5; 63.5; 40.3; 36.7 and 24.2; wherein the spectrum of Form C is measured at a temperature of about 280 K.

In one embodiment, crystalline Form C of Compound (I) is characterized by a $^{13}C$ ssNMR spectrum comprising six or more chemical shift values in ppm (all±0.2) selected from: 177.8; 163.2; 159.8; 151.2; 146.3; 136.0; 132.9; 127.0; 124.7; 123.8; 121.1; 97.5; 63.5; 40.3; 36.7 and 24.2; wherein the spectrum of Form C is measured at a temperature of about 280 K.

In one embodiment, crystalline Form C of Compound (I) is characterized by (i) a powder x-ray diffraction pattern comprising the 2θ values in degrees (CuKα) at 7.8±0.2 and 9.5±0.2; measured at a temperature of about 25° C.; and (ii) a variable endotherm at about 220° C.

In one embodiment, crystalline Form C of Compound (I) is characterized by an observed powder x-ray diffraction pattern substantially as shown in FIG. 1.

In one embodiment, crystalline Form C of Compound (I) is characterized by a variable endotherm at about 220° C.

Figure 2:
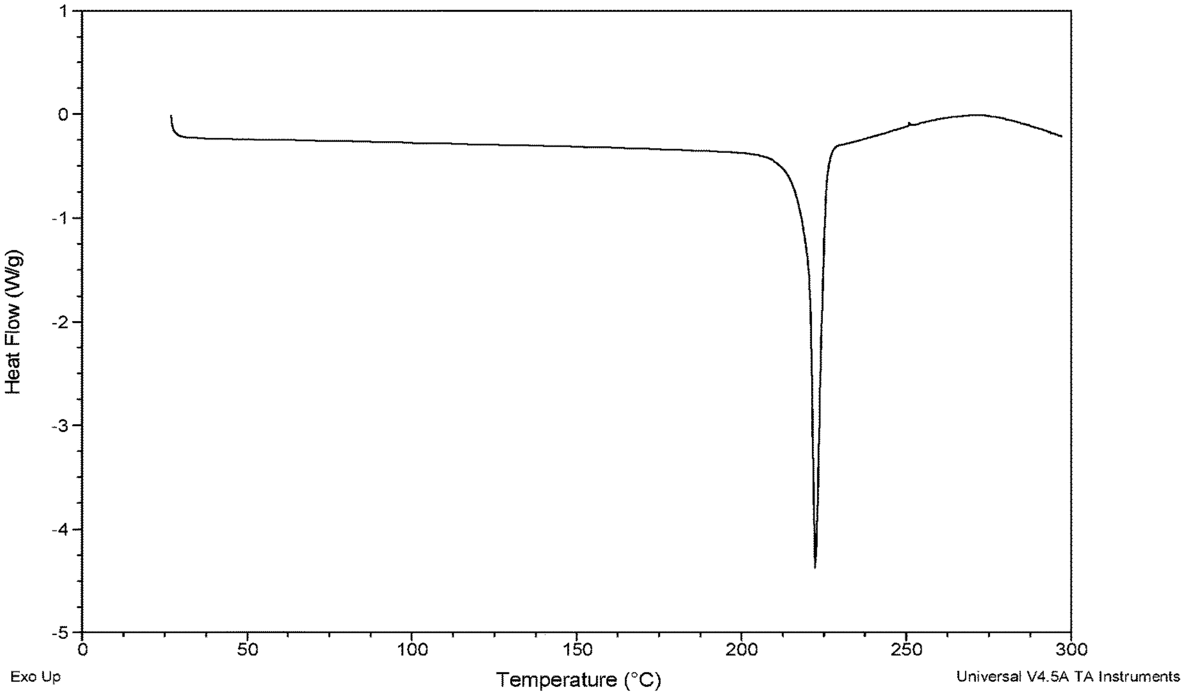
FIG. 2 shows a differential scanning calorimetry (DSC) thermogram of crystalline Form C of Compound (I).

In one embodiment, crystalline Form C of Compound (I) is characterized by a differential scanning calorimetry (DSC) thermogram substantially as shown in FIG. 2.

In one embodiment, crystalline Form C of Compound (I) is characterized by (i) a powder x-ray diffraction pattern comprising the 2θ values in degrees (CuKα) at 7.8±0.2 and 9.5±0.2, measured at a temperature of about 25° C.; and (ii) a differential scanning calorimetry (DSC) thermogram substantially in accordance with that shown in FIG. 2.

In one embodiment, crystalline Form C of Compound (I) is characterized by a thermogravimetric analysis (TGA) thermogram having weight loss of 0.2% or less based on the weight of the sample of Form C, upon being heated to a temperature of about 150° C.

Figure 3:
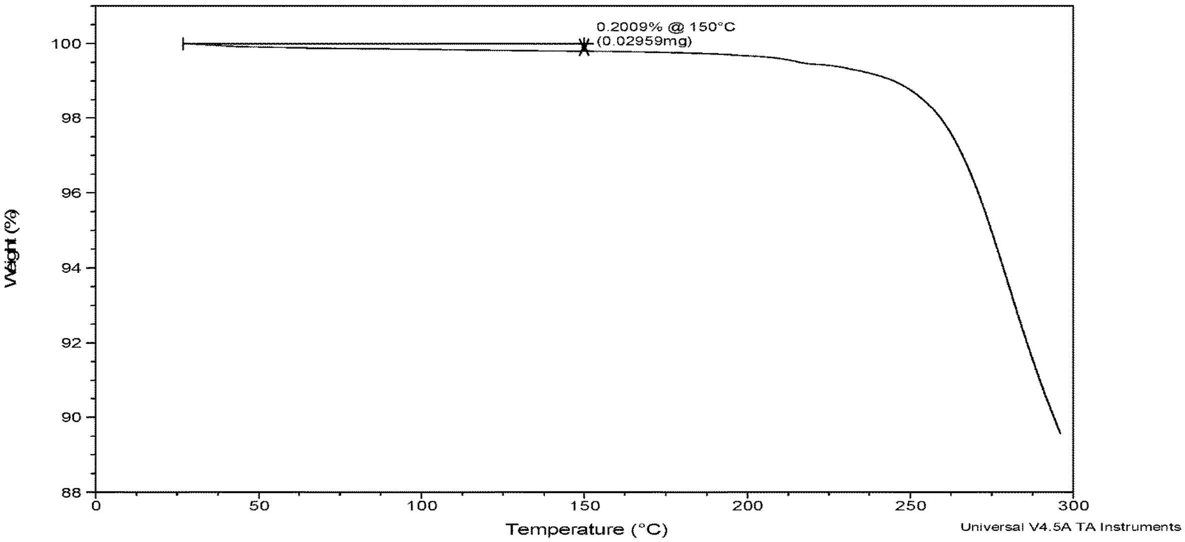
FIG. 3 shows a thermogravimetric analysis (TGA) thermogram of Form C of Compound (I).

In one embodiment, crystalline Form C of Compound (I) exhibits a thermogravimetric analysis (TGA) thermogram substantially as shown in FIG. 3.

In still yet an even further embodiment, crystalline Form C of Compound (I) is substantially pure.

In another embodiment, the crystalline form of Compound (I) consists essentially of Form C. The crystalline form of this embodiment may comprise at least about 90 wt. %, preferably at least about 95 wt. %, and more preferably at least about 99 wt. %, based on the weight of the crystalline form, Form C of Compound (I).

One embodiment provides a composition comprising 6-(cyclopropane carboxamido)-4-((2-methoxy-3-(1-methyl-1H-1,2,4-triazol-3-yl)phenyl) amino)-N-(methyl-$d_3$)pyridazine-3-carboxamide, wherein at least 95 wt. %, preferably at least 97 wt. %, and more preferably at least 99 wt. % of said 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide is in crystalline Form C.

Form D of Compound (I)

In one embodiment, Compound (I) is provided as a crystalline material comprising Form D. The crystalline Form D of Compound (I) is a sulfate salt.

In one embodiment, crystalline Form D of Compound (I) is characterized by unit cell parameters approximately equal to the following:

$a$=8.49±0.05 Å

$b$=12.39±0.05 Å

$c$=12.52±0.05 Å

α=63.0±0.5°

β=80.5±0.5°

γ=81.4±0.5°

Space group: P-1

Molecules per unit cell (Z): 2

Unit cell volume=1153±10 $Å^3$

Calculated density 1.508 $g/cm^3$ wherein the unit cell parameters of Form D of Compound (I) are measured at a temperature of about 25° C.

In one embodiment, crystalline Form D of Compound (I) is characterized by a powder x-ray diffraction pattern comprising four or more 2θ values in degrees (CuKα) selected from: 8.5±0.2; 14.4±0.2; 14.8±0.2; 17.0±0.2; 18.3±0.2; 21.9±0.2; and 27.9±0.2, wherein the PXRD pattern of Form D is measured at a temperature of about 25° C.;

In one embodiment, crystalline Form D of Compound (I) is characterized by a powder x-ray diffraction pattern comprising five or more 2θ values in degrees (CuKα) selected from: 8.5±0.2; 14.4±0.2; 14.8±0.2; 17.0±0.2; 18.3±0.2; 21.9±0.2; and 27.9±0.2, wherein the PXRD pattern of Form D is measured at a temperature of about 25° C.;

In one embodiment, crystalline Form D of Compound (I) is characterized by a powder x-ray diffraction pattern comprising six or more 2θ values in degrees (CuKα) selected from: 8.5±0.2; 14.4±0.2; 14.8±0.2; 17.0±0.2; 18.3±0.2; 21.9±0.2; and 27.9±0.2, wherein the PXRD pattern of Form D is measured at a temperature of about 25° C.;

In one embodiment, crystalline Form D of Compound (I) is characterized by a powder x-ray diffraction pattern comprising 2θ values in degrees (CuKα) at 8.5±0.2 and 18.3±0.2; and three or more 2θ values in degrees (CuKα) selected from: 14.4±0.2; 14.8±0.2; 17.0±0.2; 21.9±0.2; and 27.9±0.2; wherein the PXRD pattern of Form D is measured at a temperature of about 25° C.

In one embodiment, crystalline Form D of Compound (I) is characterized by (i) a powder x-ray diffraction pattern comprising the 2θ values in degrees (CuKα) at 8.5±0.2 and 18.3±0.2; measured at a temperature of about 25° C.; and (ii) a variable endotherm with peak max at about 233° C.

Figure 4:
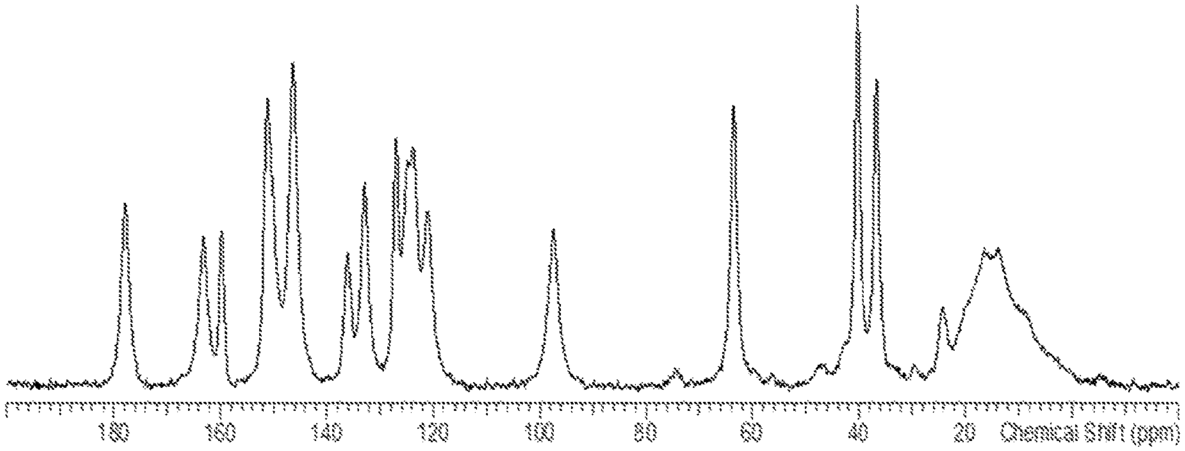
FIG. 4 shows the $^{13}C$ solid-state nuclear magnetic resonance (ssNMR) spectrum (at 280 K) of Form C of Compound (I).

In one embodiment, crystalline Form D of Compound (I) is characterized by an observed powder x-ray diffraction pattern substantially as shown in FIG. 4.

In one embodiment, crystalline Form D of Compound (I) is characterized by a variable endotherm with peak max at about 233° C.

Figure 5:
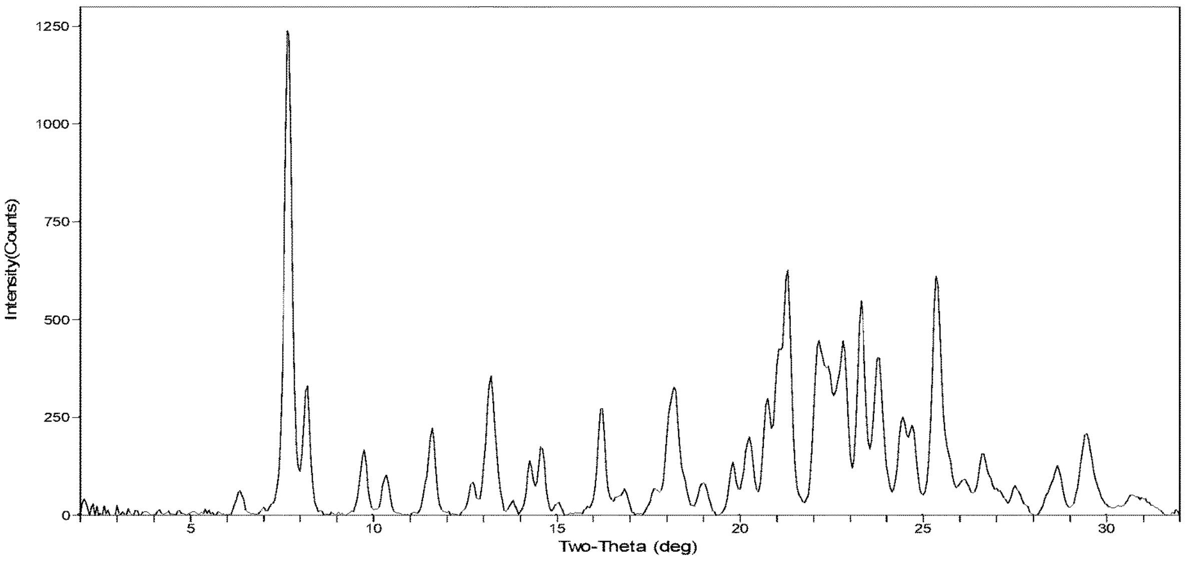
FIG. 5 shows the observed powder x-ray diffraction pattern (CuKα, at T=25° C.) of crystalline Form D of Compound (I).

In one embodiment, crystalline Form D of Compound (I) is characterized by a differential scanning calorimetry (DSC) thermogram substantially as shown in FIG. 5.

In one embodiment, crystalline Form D of Compound (I) is characterized by (i) a powder x-ray diffraction pattern comprising the 2θ values in degrees (CuKα) at 8.5±0.2 and 18.3±0.2, measured at a temperature of about 25° C.; and (ii) a differential scanning calorimetry (DSC) thermogram substantially in accordance with that shown in FIG. 5.

Figure 6:
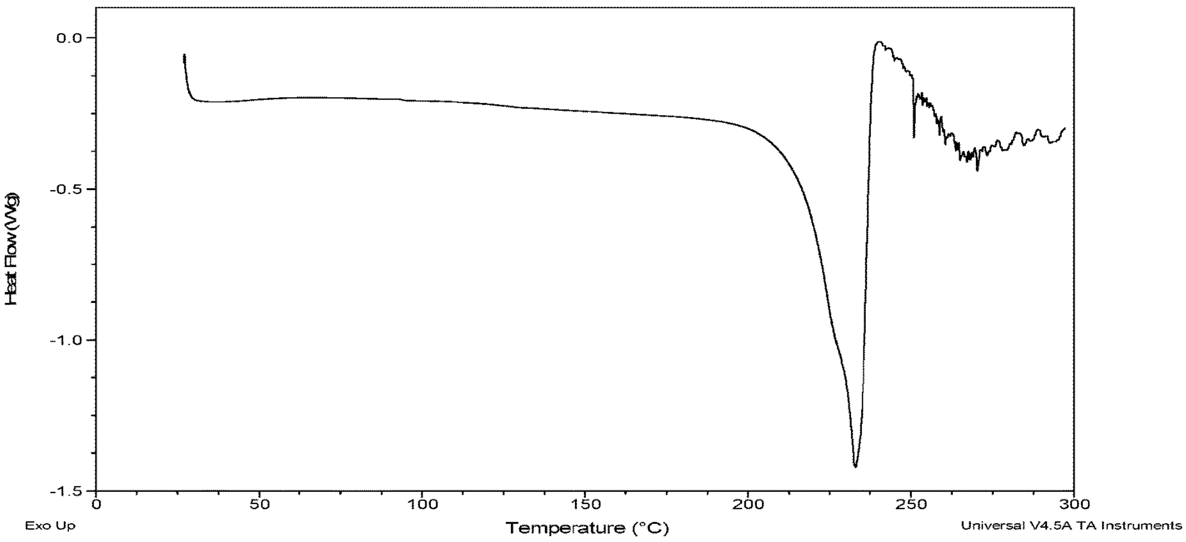
FIG. 6 shows a differential scanning calorimetry (DSC) thermogram of crystalline Form D of Compound (I).
Figure 7:
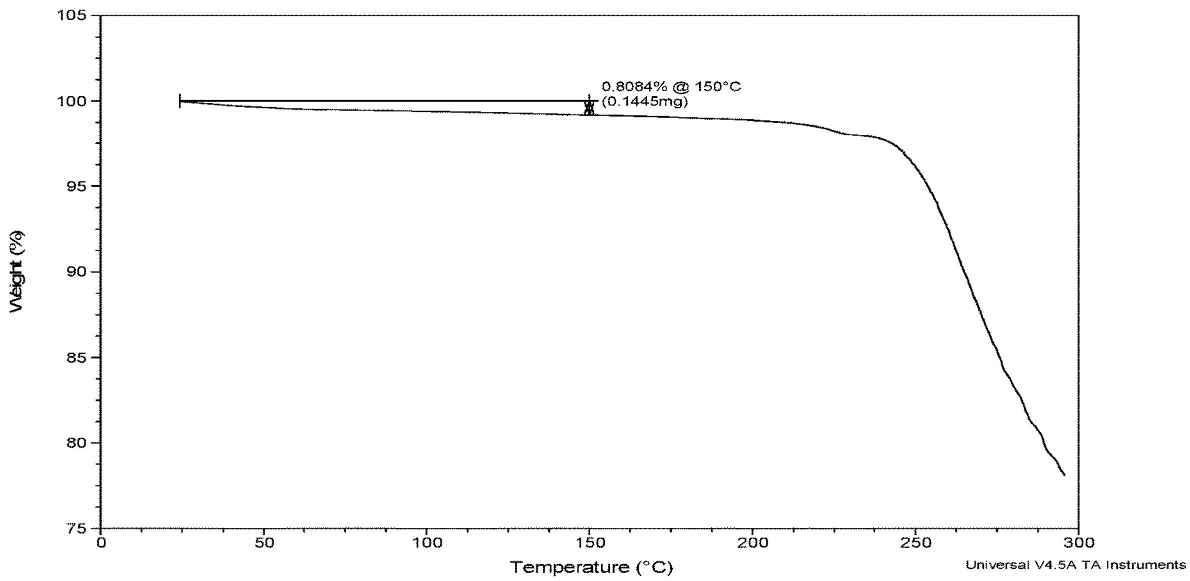
FIG. 7 shows a thermogravimetric analysis (TGA) thermogram of Form D of Compound (I).

In one embodiment, crystalline Form D of Compound (I) exhibits a thermogravimetric analysis (TGA) thermogram substantially as shown in FIG. 6.

In still yet an even further embodiment, crystalline Form D of Compound (I) is substantially pure.

In another embodiment, the crystalline form of Compound (I) consists essentially of Form D. The crystalline form of this embodiment may comprise at least about 90 wt. %, preferably at least about 95 wt. %, and more preferably at least about 99 wt. %, based on the weight of the crystalline form, Form D of Compound (I).

One embodiment provides a composition comprising 6-(cyclopropane carboxamido)-4-((2-methoxy-3-(1-methyl-1H-1,2,4-triazol-3-yl)phenyl)amino)-N-(methyl-$d_3$) pyridazine-3-carboxamide, wherein at least 95 wt. %, preferably at least 97 wt. %, and more preferably at least 99 wt. % of said 6-(cyclopropanecarboxamido)-4-((2-methoxy-3-(1-methyl-1H-1,2,4-triazol-3-yl)phenyl) amino)-N-(methyl-$d_3$)pyridazine-3-carboxamide is in crystalline Form D.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Indiana (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971, 26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid-state nuclear magnetic resonance, differential scanning calorimetry, powder x-ray diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound (I). This may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one polymorph in a sample may be determined by techniques such as powder x-ray diffraction (PXRD) or solid-state nuclear magnetic resonance (ssNMR) spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data. see Smith, D. K., "*A FORTRAN Program for Calculating X-Ray Powder Diffraction Patterns*," Lawrence Radiation Laboratory, Livermore, California, UCRL-7196 (April 1963).

Forms C & D of Compound (I) may be characterized using various techniques, the operation of which are well known to those of ordinary skill in the art. The forms may be characterized and distinguished using single crystal x-ray diffraction, which is based on unit cell measurements of a single crystal at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, another means of characterizing the crystalline structure is by powder x-ray diffraction analysis in which the diffraction profile is compared to a simulated profile representing pure powder material, both run at the same analytical temperature, and measurements for the subject form characterized as a series of 2θ values in degrees (usually four or more).

Other means of characterizing the form may be used, such as solid-state nuclear magnetic resonance, differential scanning calorimetry, thermal analysis, and vibrational spectroscopy. These parameters may also be used in combination to characterize the subject form.

Utility

Crystalline Forms C and D of Compound (I) can be used to isolate Compound (I) from other components at the completion of the synthesis process; and/or to purify Compound (I) by one or a series of crystallization steps. The isolation and the purification steps can be combined or practiced as separate process steps.

EXAMPLE

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention as defined by the claims appended hereto.

For ease of reference, the following abbreviations may be used herein.

Abbreviations

| Abbreviation | Name |
|---|---|
| ACN or MeCN | Acetonitrile |
| AcOH | acetic acid |
| AP | area percent |
| aq. | Aqueous |
| BuOAc | butyl acetate |
| conc. | Concentrated |
| DBU | 1,8-diazabicyclo[5.4.0]undec-7-ene |
| DCM | dichloromethane |
| DIPEA | N,N-diisopropylethylamine (Hunig's base) |
| DMA | dimethylacetamide |
| EDC HCl | 1-(dimethylaminopropyl)-3-ethylcarbodiimide hydrochloride |
| equiv. | molar equivalents |
| Et | ethyl |
| EtOAc | ethyl acetate |
| h | hour(s) |
| HIL | High intensity light |
| HOBt | 1-hydroxy benzotriazole |
| HPLC | high pressure liquid chromatography |
| IPA | isopropyl alcohol |
| M | molar |
| min | minute(s) |
| Me | methyl |
| mg | milligram |
| mL | milliliter |
| NaOH | sodium hydroxide |
| MTBE | methyl tert-butyl ether |
| NMI | N-methyl-imidazole |
| NMP | n-methylpyrrolidone |
| NMR | nuclear magnetic resonance |
| $Pd_2(dba)_3$ | tris-(dibenzylideneacetone)dipalladium |
| Pd/C | palladium on carbon |
| RH | Relative humidity |
| rt/RT | room temperature |
| sat. | saturated |
| t-BuOK | potassium tert-butoxide |
| TEA | triethanolamine |
| THF | tetrahydrofuran |
| TsCl | p-toluenesulfonyl chloride |
| XANTPHOS | 4,5-bis(diphenylphosphino)-9,9 dimethylxanthene |
| 2-Me THF | 2-methyl tetrahydrofuran |

Example 1: Preparation of Crystalline Form C of Compound (I)

A solution was prepared by mixing 360 mg of Compound I into 23 mL THF and 1 mL water at room temperature (25° C.) until fully solubilized into which 55 μL of Methanesulfonic acid was added. The resulting slurry was dried overnight using a Speedvac. The 90 mg of the dried solid was suspended in 1 ml of BuOAc at 60° C. and the resulting slurry was aged at 60° C. overnight. The slurry was filtered and the wet cake was dried in a vacuum oven at a temperature in the range of 50-60° C. to afford Compound I in Form C.

Example 2: Preparation of Crystalline Form C of Compound (I)

A solution was prepared by mixing 550 mg of Compound I into 35 mL THF and 2 mL water at room temperature (25° C.) until fully solubilized into which 84 μL of Methanesulfonic acid was added. The resulting slurry was dried overnight using a Speedvac. The dried solid was suspended in 5 ml of BuOAc at 60° C. and the resulting slurry was aged at 60° C. overnight. The slurry was filtered and the wet cake was dried in a vacuum oven at a temperature in the range of 50-60° C. to afford Compound I in Form C.

Example 3: Preparation of Crystalline Form D of Compound (I)

A solution was prepared by mixing 50 mg of Compound I and 0.5 ml of 0.25 M $H_2SO_4$ into 2 ml of acetone and heating to 55° C. The mixture was stirred overnight at 55° C., after which the heat was turned off left overnight at room temperature without stirring which resulted in crystals of Form D.

Example 4: Preparation of Crystalline Form D of Compound (I)

A solution was prepared by mixing 550 mg of Compound I into 35 mL THF and 2 mL water at room temperature (25° C.) until fully solubilized into which 72 μL of 96% $H_2SO_4$ was added. The resulting slurry was dried overnight using a Speedvac. The dried solid was suspended in 5 ml of BuOAc at 60° C. and the resulting slurry was aged at 60° C. overnight. The slurry was filtered and the wet cake was dried in a vacuum oven at a temperature in the range of 50-60° C. to afford Compound I in Form D.

Form C

PXRD

X-ray powder diffraction (PXRD) data were obtained using a Bruker C2 GADDS with Vantec-500 detector. The radiation was Cu Kα (40 KV, 40 mA). The sample-detector distance was ~20 cm. Incident optics include Goebel mirror and 0.3 mm collimator. Powder samples were placed in sealed glass capillaries of 1 mm or less in diameter; the capillary was rotated during data collection. Data were collected for $2 \leq 2\theta \leq 35°$ with a sample exposure time of at least 1000 seconds. The resulting two-dimensional diffraction arcs were integrated to create a traditional 1-dimensional PXRD pattern with a step size of 0.05 degrees 2θ in the range of ~2 to ~30 degrees 2θ.

DSC

Differential scanning calorimetry (DSC) experiments were performed in a TA Instruments™ model Q1000. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA

Thermal gravimetric analysis (TGA) experiments were performed in a TA Instruments™ model Q500. The sample (about 10-30 mg) was placed in a platinum pan previously tared. The weight of the sample was measured accurately and recorded to a thousand of a milligram by the instrument.

The furnace was purged with nitrogen gas at 100 mL/min. Data were collected between room temperature and 300° C. at 10° C./min heating rate.

Solid-State Nuclear Magnetic Resonance (ssNMR)

Carbon-13 cross polarization magic angle spinning (CPMAS) solid-state NMR experiments were conducted on a Bruker AV III instrument operating at a proton frequency of 500 MHz. Solid samples were spun at 13 kHz in a 4 mm $ZrO_2$ rotor. The contact time was 4 milliseconds and was ramped on the proton channel from 50 to 100% (A. E. Bennett et al, *J. Chem. Phys.*, 1995, 103, 6951), (G. Metz, X. Wu and S. O. Smith, *J. Magn. Reson. A.*, 1994, 110, 219-227). The relaxation delay was maintained at 5× $^1H$ $T_1$ of API, which was 9.1 seconds. Proton decoupling was applied using a TPPM sequence with a 4.2 microsecond pulse (59.5 kHz nominal bandwidth). The spectral sweep width was 300 ppm centered at 100 ppm. 4 380 data points were acquired (giving a digital resolution of 20 Hz) and zero filled to 8192 prior to apodization with 20 Hz line broadening. 1024 free induction decays were co-added. The spectra were referenced indirectly to TMS using 3-methylglutaric acid (D. Barich, E. Gorman, M. Zell, and E. Munson, *Solid State Nuc. Mag. Res.*, 2006, 30, 125-129). Approximately 70 mg of sample was used for each experiment. The temperature was set to 280 K.

FORM D

Single Crystal Data

Single crystal X-ray data was collected using a Bruker X8-Proteum diffractometer equipped with a APEX II CCD detector and a MICROSTAR microfocus rotating anode X-ray generator of monochromatic Cu Kα radiation. The single crystal was at room temperature (approximately 25° C.) during data collection.

The final unit cell parameters were obtained from least-squares refinement using the setting angles of 6414 reflections in the range 3.99°<θ<60.10°. The structures were solved by direct methods using the SHELXS-97 software and refined by full-matrix least-squares approach using the SHELXL-97 software (Sheldrick, G. M. (2015). Acta Cryst. C71, 3-8.). Structure refinements involved minimization of the function defined by $\Sigma w(|F_o|-|F_c|)^2$, where w is an appropriate weighting factor based on errors in the observed intensities, $F_o$ is the structure factor based on measured reflections, and $F_c$ is the structure factor based on calculated reflections. Agreement between the refined crystal structure model and the experimental X-ray diffraction data is assessed by using the residual factors $R=\Sigma||F_o|-|F_c||/\Sigma|F_o|$ and $wR=[\Sigma w(|F_o|-|F_c|)^2/\Sigma w|F_o|]^{1/2}$. Difference Fourier maps were examined at all stages of refinement. All non-hydrogen atoms were refined with anisotropic thermal displacement parameters. Hydrogen atoms were refined independently.

PXRD

X-ray powder diffraction (PXRD) data were obtained using a Bruker C2 GADDS with Vantec-500 detector. The radiation was Cu Kα (40 KV, 40 mA). The sample-detector distance was ~20 cm. Incident optics include Goebel mirror and 0.3 mm collimator. Powder samples were placed in sealed glass capillaries of 1 mm or less in diameter; the capillary was rotated during data collection. Data were collected for 2≤2θ≤35° with a sample exposure time of at least 1000 seconds. The resulting two-dimensional diffraction arcs were integrated to create a traditional 1-dimensional PXRD pattern with a step size of 0.05 degrees 2θ in the range of ~2 to ~30 degrees 2θ.

DSC

Differential scanning calorimetry (DSC) experiments were performed in a TA Instruments™ model Q1000. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

TGA

Thermal gravimetric analysis (TGA) experiments were performed in a TA Instruments™ model Q500. The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

We claim:

1. Crystalline Form C of 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide, wherein said Form C is characterized by a powder x-ray diffraction (PXRD) pattern comprising 2θ values in degrees (CuKα) at 7.1±0.2; 7.8±0.2; and 9.5±0.2; wherein the PXRD pattern is measured at a temperature of about 25° C.

2. The crystalline form according to claim 1, wherein the PXRD pattern further comprises one or more 2θ values in degrees (CuKα) selected from 10.6±0.2; 11.4±0.2; 12.8±0.2; 15.6±0.2; 17.5±0.2; and 24.1±0.2.

3. The crystalline form according to claim 1, wherein the PXRD pattern further comprises two or more 2θ values in degrees (CuKα) selected from 10.6±0.2; 11.4±0.2; 12.8±0.2; 15.6±0.2; 17.5±0.2; and 24.1±0.2.

4. The crystalline form according to claim 1, wherein said Form C is further characterized by a $^{13}C$ ssNMR spectrum comprising four or more chemical shift values in ppm (all ±0.2) selected from: 177.8; 163.2; 159.8; 151.2; 146.3; 136.0; 132.9; 127.0; 124.7; 123.8; 121.1; 97.5; 63.5; 40.3; 36.7 and 24.2; wherein the $^{13}C$ ssNMR spectrum is measured at a temperature of about 280° K.

5. The crystalline form according to claim 1, wherein said Form C is further characterized by an observed powder x-ray diffraction pattern substantially as shown in FIG. 1.

6. A crystalline compound consisting essentially of the crystalline form according to claim 1.

7. The crystalline form according to claim 5, wherein said crystalline form has a purity greater than 90 weight %.

8. A composition comprising 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide, wherein at least 90 weight % of said 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide is in the crystalline form according to claim 1.

9. A composition comprising 6-(cyclopropanecarboxamido)-4-((2-methoxy-3-(1-methyl-1H-1,2,4-triazol-3-yl) phenyl)amino)-N-(methyl-$d_3$)pyridazine-3-carboxamide, wherein at least 95 weight % of said 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide is in the crystalline form according to claim 1.

10. A composition comprising 6-(cyclopropanecarboxamido)-4-((2-methoxy-3-(1-methyl-1H-1,2,4-triazol-3-yl) phenyl)amino)-N-(methyl-$d_3$)pyridazine-3-carboxamide, wherein at least 90 weight % of said 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide is in the crystalline form according to claim 2.

11. 6-(cyclopropanecarboxamido)-4-((2-methoxy-3-(1-methyl-1H-1,2,4-triazol-3-yl)phenyl)amino)-N-(methyl-$d_3$) pyridazine-3-carboxamide, wherein at least 95 weight % of said 6-(cyclopropanecarboxamido)-4-((2-methoxy-3-(1-methyl-1H-1,2,4-triazol-3-yl)phenyl)amino)-N-(methyl-$d_3$) pyridazine-3-carboxamide is in the crystalline form according to claim 2.

12. A composition comprising 6-(cyclopropanecarboxamido)-4-((2-methoxy-3-(1-methyl-1H-1,2,4-triazol-3-yl) phenyl)amino)-N-(methyl-$d_3$)pyridazine-3-carboxamide, wherein at least 90 weight % of said 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide is in the crystalline form according to claim 5.

13. A composition comprising 6-(cyclopropanecarboxamido)-4-((2-methoxy-3-(1-methyl-1H-1,2,4-triazol-3-yl) phenyl)amino)-N-(methyl-$d_3$)pyridazine-3-carboxamide, wherein at least 95 weight % of said 6-(cyclopropanecarboxamido)-4-((2-methoxy-3-(1-methyl-1H-1,2,4-triazol-3-yl)phenyl)amino)-N-(methyl-$d_3$)pyridazine-3-carboxamide is in the crystalline form according to claim 5.

* * * * *